United States Patent [19]

Eastman

[11] Patent Number: 4,990,628
[45] Date of Patent: Feb. 5, 1991

[54] CATALYTIC PREPARATION OF THIOLACTAMS

[75] Inventor: Alan D. Eastman, Bartlesville, Okla.

[73] Assignee: Phillips Petroleum Company, Bartlesville, Okla.

[21] Appl. No.: 486,710

[22] Filed: Mar. 1, 1990

[51] Int. Cl.$^5$ ............... C07D 207/267; C07D 211/76; C07D 223/10
[52] U.S. Cl. .................................. 548/543; 546/243; 540/533
[58] Field of Search ...................... 548/543; 546/243; 540/533

[56] References Cited

U.S. PATENT DOCUMENTS

| | | | |
|---|---|---|---|
| 3,306,910 | 2/1967 | Louthan | 546/243 X |
| 3,306,911 | 2/1967 | Doss | 260/326.83 |
| 3,632,605 | 1/1972 | Debarre et al. | 260/326.5 |
| 4,145,352 | 3/1979 | Kubicek | 548/543 |

Primary Examiner—David B. Springer
Attorney, Agent, or Firm—K. K. Brandes

[57] ABSTRACT

The reaction of lactams (preferably N-methyl-2-pyrrolidone) with hydrogen sulfide to thiolactams (preferably N-methyl-2-thiopyrrolidone) is conducted in the presence of a catalyst comprising an alumina-supported Group VIII metal or Group VIII metal compound (preferably palladium metal/oxide and/or iron oxide).

20 Claims, No Drawings

CATALYTIC PREPARATION OF THIOLACTAMS

BACKGROUND OF THE INVENTION

This invention relates to the catalytic conversion of hydrogen sulfide and lactams (cyclic amides) to thiolactams. In a particular aspect, this invention relates to the catalytic reaction of N-methyl-2-pyrrolidone with hydrogen sulfide to N-methyl-2-thiopyrrolidone (also referred to as N-methylpyrrolidine-2-thione).

The catalytic conversion of lactams (in particular N-methyl-2-pyrrolidone) and $H_2S$ to thiolactams (in particular N-methyl-2-thiopyrrolidone) is known and has been described in U.S. Pat. No. 4,145,352, the entire disclosure of which is incorporated herein by reference. As has been pointed out in this patent, N-methyl-2-thiopyrrolidone can be used as a sulfur source in the preparation of polymenylene sulfide). The instant invention is directed to an improvement of the process of U.S. Pat. No. 4,145,352 by employing a more effective catalyst.

SUMMARY OF THE INVENTION

It is an object to prepare thiolactams by the catalytic reaction of lactams with hydrogen sulfide. It is another object of this invention to prepare N-methyl-2-thiopyrrolidone from N-methyl-2-pyrrolidone and $H_2S$. Other objects and advantages will become apparent from the detailed disclosure and the appended claims.

In accordance with this invention, in a process for reacting at least one lactam with hydrogen sulfide so as to produce at least one thiolactam, the improvement comprises employing a catalyst composition comprising alumina (as support material) and at least one Group VIII metal or at least one compound (preferably oxide) thereof, more preferably platinum metal and/or oxide or iron oxide, deposited on said alumina. Group VIII of the Periodic Table contains iron, cobalt, nickel, ruthenium, rhodium, palladium, osmium, iridium and platinum.

DETAILED DESCRIPTION OF THE INVENTION

Any suitable lactam (cyclic amide) can be employed as reactant in the process of this invention. These lactams are represented by the structural formula.

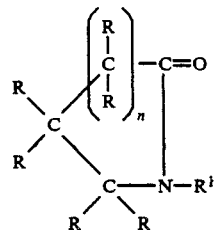

wherein each R and $R^1$ is independently selected from the group consisting of hydrogen, alkyl radicals and cycloalkyl radicals, and combinations thereof, preferably containing from 1 to 6 carbon atoms; and n can be an integer in the range of from 0 to 10. The total number of carbon atoms in these lactams generally should not exceed 20.

Lactams which can be converted to thiolactams by the process of this invention include 2-azetidinone, 2-pyrrolidone, 2-piperidone, 2-oxohexamethylenimine(-caprolactam), N-methyl-2-azetidinone, N-methyl-2-pyrrolidone, N-ethyl-2-pyrrolidone, N-propyl-2-pyrrolidone, 2-oxo-1-ethylhexamethylenimine, 3,3-di-n-propyl-2-piperidone, 2-oxo-4-n-hexyl-hexamehtylenimine, 2-oxo-2-cyclopentylhexamethylenimine, lactam of 7-(cyclohexylamino)-heptanoic acid, lactam of 13-aminotridecanoic acid, 3,4,5-tri-n-pentyl-2-piperidone, 3-cyclopentyl-2-pyrrolidone, lactam of 3-amino-3-cyclohexyl-4-ethyloctanoic acid, 1-isopropyl-2-pyrrolidone, 2-oxo-1-ethyl-3-tert-butylhexamethylenimine, and the like. Preferred lactams are N-alkyl-2-pyrrolidones with the alkyl group containing 1-3 carbon atoms; in particular N-methyl-2-pyrrolidone.

The thiolactams which are prepared by this invention are represented by the formula:

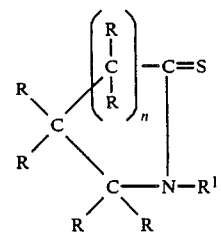

wherein R, R' and n are as defined above (for lactams).

The preferred thiolactams are N-alkyl-2-thiopyrrolidones with the alkyl group containing 1-3 carbon atoms, in particular N-methyl-2-thiopyrrolidone.

The catalyst composition which is employed in the process of this invention contains alumina as support material. Preferably, the support material consists essentially of alumina. Any suitable alumina-containing material (many of which are commercially available) can be employed as catalyst. The method of preparation of alumina is not considered critical. Generally, first hydroxides and/or hydrated oxides of aluminum are precipitated from an aqueous solution of a dissolved aluminum compound by means of a suitable alkaline substance (e.g., aqueous $NH_3$). Then the precipitate is separated, washed, and finally heated (calcined) so as to remove water therefrom and to convert the hydroxide to an oxide of aluminum, preferably chi-alumina or eta-alumina of gamma-alumina or combinations thereof.

The surface area (determined by the BET method employing $N_2$; substantially in accordance with ASTM D3037) of alumina should exceed about 10 m$^2$/g, and generally is in the range of from about 10 to about 400 m$^2$/g. The alumina containing particles, which are used as support material, can have spherical, trilobal, quadrilobal or irregular shape. Preferably, impurities should be substantially absent from the alumina support material (i.e., they should not be present at a level higher than about 2 weight-%, preferably less than about 0.5 weight-%).

The Group VIII metal promoter component of the catalyst composition employed in the process of this invention can be any metal and/or compound (preferably oxide) of a metal selected from the group consisting of Fe, Co, Ni, Ru, Rh, Pd, Os, Ir, or mixtures of two or more than two metals and/or their compounds. One preferred promoter is palladium metal or oxide or a mixture thereof. Another preferred promoter is iron oxide (i.e., FeO and/or $Fe_2O_3$ and/or $Fe_3O_4$). Generally the amount of the promoter, expressed as metal, in the dry catalyst composition is in the range of from about 0.01 to about 10 weight-% Group VIII metal (preferably Pd or Fe), preferably in the range of from about 0.2 to about 5 weight-% Pd or Fe. It is within the scope of this invention to have both Pd and Fe present with a promoter level of about 0.01–10 weight-% Pd and about 0.01–10 weight-% Fe.

The catalyst composition used in the process of this invention can be prepared by any suitable means. Generally, an alumina containing material (described above; preferably consisting essentially of alumina) is impregnated with a solution of at least one compound of at least one Group VIII metal (preferably Pd or Fe), e.g., by incipient wetness impregnation or by spraying of the solution onto the alumina containing material. Suitable Pd compounds include $Pd(NO_3)_2$, $Pd(NH_3)_4(NO_3)_2$. $Pd(NH_3)_4(NO_2)_2$ and the like. Suitable Fe compounds include $Fe(NO_3)_2$. $Fe_2(NO_3)_3$, $FeSO_4$, $Fe_2(SO_4)_3$, $NH_4Fe(SO_4)_2$, Fe acetylacetonate and the like. The concentration of the Group VIII metal compound in the impregnating solution, and the weight ratio of this solution to the support material are chosen so as to provide the Group VIII metal promoter level recited above.

Thereafter the material is heated at a temperature high enough (preferably about 200–700° C.) to substantially dry the catalyst composition and to at least partially decompose the GROUP VIII metal compound(s) to Group VIII metal oxide(s). Optionally, the substantially dried material can be heated in a reducing gas atmosphere (e.g., at about 200–600° C., preferably with hydrogen gas or carbon monoxide), in particular when the Group VIII metal is Pd, so as to reduce at least a portion of palladium oxide to the metallic form. The surface area and shape of the finished catalyst composition is approximately the same as the surface area and shape of the alumina-containing support material, described above.

The reaction conditions for the catalyzed preparation of thiolactams described herein are considered to be mild. Generally, the reaction is carried out at an elevated temperature of about 500–800° F., with a preferred range of about 500° to about 700° F. (about 260°–371° C.). The reaction can be carried out at a pressure ranging from about 1 to about 1000 psia, with a preferred pressure range of about 7 to about 150 psia (about 0.5–10 atm).

Although the invention is operable over a broad range of molar ratios of the reactants and with a broad range of feed rates, the usual range of the molar ratio of $H_2S$ to lactam in the feed is about 2:1 to about 20:1, with a preferred range of about 3:1 to about 12:1. It is understood that $H_2S$ and lactam can be introduced simultaneously but separately into the reaction zone, or they can be introduced together in one feed stream. The weight hourly space velocity of the lactam will generally be in the range of from about 1 to about 200 g lactam/g catalyst/hour, preferably about 2–200 g/g/hour.

The formed thiolactam can be separated from unconverted reactants lactam and $H_2S$) and from by-products, such as water (which is also formed in the reaction), by any suitable separating means, such as fractional distillation, and can then be recovered. Unconverted lactam and $H_2S$ can be recycled to the reaction zone. The reaction of this invention and the subsequent separation steps can be carried out as batch operations or continuously (the latter being preferred).

The following example is presented in further illustration of the invention and are not to be considered as unduly limiting the scope of this invention.

EXAMPLE

This example illustrates the reaction of N-methyl-2-pyrrolidone (NMP) with $H_2S$ to N-methyl-2-thiopyrrolidone (TNMP) and water, in the presence of alumina-supported Group VIII metal catalysts.

A tubular stainless steel reactor of 80 cc internal volume was charged with a support layer of inert α-alumina (Alundum ®; surface area: about 1 m²/g), a layer of 10 cc of a catalyst, and a top layer of Alundum ®. The reactor was heated to the desired reaction temperature by means of three-zone electrical furnace. $H^2S$ gas was introduced through an inlet tube at the reactor top, generally at a gas hourly space velocity (GHSV) of about 1,800–2,500 cc $H_2S$ per cc catalyst. Liquid NMP was introduced through another inlet tube at the reactor top, generally at a weight hourly space velocity of about 3–10 g NMP per g catalyst per hour. The gaseous effluent was analyzed by means of a gas chromatograph.

The following catalysts were tested:

(A) 0.5 weight-% Pd on Catapal alumina, provided by United Catalysts Inc. (UCI), Louisville, Ky., under the product designation L-3664;

(B) 0.5 weight-% Pd on Catapal alumina, provided by UCI under the product designations L-119;

(C) 0.5 weight-% Pd on Catapal alumina, provided by UCI under the product designation L-120;

(D) 0.5 weight-% Pd on Catapal alumina, provided by UCI under the product designation L-100;

(E) 0.3 weight-% Pd on alumina, provided by Calsicat, Inc., Erie, Pa., under the product designation 42C-26B;

(F) a "skin catalyst" containing 0.5 weight-% Pd (located in the skin region) on alumina, provided by UCI under the product designation T-2464;

(G) a "skin catalyst" containing 0.5 weight-% Pd (located in the shell region) on alumina spheres, provided by Calsicat under the product designation E-144;

(H) a "skin catalyst" containing 0.5 weight-% Pd (located in the skin region) on alumina, provided by Engelhard Corporation, Menlo Park, N.J., under the product designation 15296-40-2;

(I) an alumina material containing 0.95 weight-% Fe (as oxide), provided by Harshaw, now a division of Englehard Corporation, under the product designation AL-0105-T; containing Ti, P and Th at levels of about 0.1 weight-% each;

(J) 1.1 weight-% Fe (as oxide) on gamma alumina extrudates as support (provided by Akzo-Katjen Catalyst Company, Pasadena, Tex.); having been prepared by impregnating the alumina extrudates of 1.5 mm diameter and 5–10 mm length with dissolved iron sulfate, followed by drying and calcining at about 600° C.;

(K) 1.9 weight-% Fe (as oxide) on S-201 alumina (provided by Kaiser Aluminum Company, Los Angeles, Calif.), having been prepared by impregnation of ⅛ inch alumina spheres substantially as described for (J);

(L) a catalyst in accordance with U.S. Pat. No. 4,145,352 comprising 5 weight-% phosphotungstic acid on alumina.

Average reaction conditions and test results (for test runs of about 40–200 hours on stream; 4–13 measurements per run) are summarized below:

TABLE

| Catalyst | Average Reaction Temp. (°F.) | Average Pressure (psia) | Average GHSV of H$_2$S | Average Molar Ratio of H$_2$S/NMP | Average Conversion of NMP (%) | Average Selectivity to TNMP (%)[1] |
|---|---|---|---|---|---|---|
| A (Pd/Al$_2$O$_3$) | 625 | 15.1 | 2360 | 8.0:1 | 20.7 | 100 |
| B (Pd/Al$_2$O$_3$) | 625 | 16.3 | 2280 | 8.2:1 | 21.5 | 100 |
| C (Pd/Al$_2$O$_3$) | 650 | 15.7 | 2320 | 8.1:1 | 16.8 | 98.3 |
| D (Pd/Al$_2$O$_3$) | 638 | 15.1 | 2350 | 8.2:1 | 24.3 | 99.2 |
| E (Pd/Al$_2$O$_3$) | 650 | 15.5 | 2320 | 8.2:1 | 13.1 | 98.8 |
| F (Pd/Al$_2$O$_3$) | 635 | 15.0 | 2370 | 8.0:1 | 16.9 | 99.3 |
| G (Pd/Al$_2$O$_3$) | 625 | 15.0 | 2370 | 8.0:1 | 5.9[2] | 77.1[2] |
| H (Pd/Al$_2$O$_3$) | 625 | 16.1 | 2290 | 8.1:1 | 20.2 | 99.6 |
| I (Fe/Al$_2$O$_3$) | 650 | 15.1 | 2360 | 7.9:1 | 23.3 | 99.2 |
| J (Fe/Al$_2$O$_3$) | 625 | 15.1 | 2360 | 8.1:1 | 14.9 | 98.7 |
| K (Fe/Al$_2$O$_3$) | 625 | 15.0 | 2360 | 8.1:1 | 10.8 | 99.7 |
| L (W/Al$_2$O$_3$; U.S. Pat. No 4,145,352) | 725 | 17.1 | 2070 | 5.0:1 | 7.8 | 79.2 |

[1] calculated on a water free basis
[2] results believed to be erroneous because of catalyst poisoning The above-summarized test results show that the use of Pd or Fe on alumina catalysts (with the questionable exception of Catalyst G) resulted in considerably higher NMP conversion and higher selectivity to thio-NMP than the use of Control Catalyst L (phosphotungstic acid on alumina; the preferred catalyst employed in the process of U.S. Pat. No. 4,145,352).

Reasonable variations and modifications are possible within the scope of the disclosure of this invention and the appended claims.

That which is claimed is:

1. In a process for reacting at least one lactam with hydrogen sulfide so as to produce at least one thiolactam, the improvement which comprises employing a catalyst comprising (i) alumina as support material and (ii) at least one Group VIII metal or compound thereof deposited on said support material.

2. A process in accordance with claim 1, wherein said alumina is selected from the group consisting of chi-alumina, eta-alumina, gamma-alumina, and combinations thereof.

3. A process in accordance with claim 2, wherein said catalyst has a surface area, determined by the BET method employing N$_2$, in excess of about 10 m$^2$/g.

4. A process in accordance with claim 1, wherein said at least one lactam is a N-alkyl-2-pyrrolidone with the alkyl group containing 1-3 carbon atoms, and the thiolactam is a N-alkyl-2-thiopyrrolidone with the alkyl group containing 1-3 carbon atoms.

5. In a process for reacting N-methyl-2-pyrrolidone with hydrogen sulfide so as to produce N-methyl-2-thiopyrrolidone, the improvement which comprises employing a catalyst comprising at least one substance selected from the group consisting of palladium metal and palladium oxide, and alumina as a support material.

6. A process in accordance with claim 5, wherein said alumina is selected from the group consisting of chi-alumina, eta-alumina, gamma-alumina, and combinations thereof.

7. A process in accordance with claim 6, wherein said catalyst has a surface area, determined in accordance with the BET method employing N$_2$, exceeds about 10 m$^2$/g.

8. A process in accordance with claim 5, wherein said catalyst contains about 0.01-10 weight-% Pd.

9. A process in accordance with claim 5, wherein said process is carried out at about 500-800° F. and a molar ratio of H$_2$S to N-methyl-2-pyrrolidone of about 2:1 to about 20:1.

10. A process in accordance with claim 5, wherein said temperature is about 600-750° F. and said molar ratio is about 3:1 to about 12:1.

11. A process in accordance with claim 5, wherein said reaction is carried out at a weight hourly space velocity of N-methyl-2-pyrrolidone of about 2 to about 2,000 g per gram catalyst per hour and a pressure of about 1 to about 1,000 psia.

12. A process in accordance with claim 5, wherein said N-methyl-2-thiopyrrolidone is recovered after having been separated from unconverted N-methyl-2-pyrrolidone, unconverted H$_2$S and formed water.

13. In a process for reacting N-methyl-2-pyrrolidone with hydrogen sulfide so as to produce N-methyl-2-thiopyrrolidone, the improvement which comprises employing a catalyst comprising iron oxide on alumina support.

14. A process in accordance with claim 13, wherein said alumina is selected from the group consisting of chi-alumina, eta-alumina, gamma-alumina, and combinations thereof.

15. A process in accordance with claim 14, wherein said catalyst has a surface area, determined in accordance with the BET method employing N$_2$, exceeds about 10 m$^2$/g.

16. A process in accordance with claim 13, wherein said catalyst contains about 0.01-10 weight-% Fe.

17. A process in accordance with claim 13, wherein said process is carried out at about 500-800° C. and a molar ratio of H$_2$S to N-methyl-2-pyrrolidone of about 2:1 to about 20:1.

18. A process in accordance with claim 13, wherein said temperature is about 600–750° F. and said molar ratio is about 3:1 to about 12:1.

19. A process in accordance with claim 13, wherein said reaction is carried out at a weight hourly space velocity of N-methyl-2-pyrrolidone of about 2 to about 2,000 g per gram catalyst per hour and a pressure of about 1 to about 1,000 psia.

20. A process in accordance with claim 13, wherein said N-methyl-2-thiopyrrolidone is recovered after having been separated from unconverted N-methyl-2-pyrrolidone, unconverted $H_2S$ and formed water.

* * * * *